(12) United States Patent
Gadonniex et al.

(10) Patent No.: US 11,074,796 B2
(45) Date of Patent: Jul. 27, 2021

(54) PHOTOELECTRIC SMOKE DETECTORS

(71) Applicant: CARRIER CORPORATION, Palm Beach Gardens, FL (US)

(72) Inventors: Dennis Michael Gadonniex, Bradenton, FL (US); Vipul Patel, Sarasota, FL (US); Paul Schatz, Bradenton, FL (US)

(73) Assignee: Carrier Corporation, Palm Beach Gardens, FL (US)

( * ) Notice: Subject to any disclaimer, the term of this patent is extended or adjusted under 35 U.S.C. 154(b) by 0 days.

(21) Appl. No.: 16/824,054

(22) Filed: Mar. 19, 2020

(65) Prior Publication Data
US 2020/0312108 A1 Oct. 1, 2020

Related U.S. Application Data

(60) Provisional application No. 62/827,612, filed on Apr. 1, 2019.

(51) Int. Cl.
*G08B 17/117* (2006.01)
*G01N 15/06* (2006.01)
*G01N 33/00* (2006.01)

(52) U.S. Cl.
CPC .......... *G08B 17/117* (2013.01); *G01N 15/06* (2013.01); *G01N 33/004* (2013.01); *G01N 2015/0693* (2013.01)

(58) Field of Classification Search
CPC .................................................. G08B 17/117
USPC .......................................................... 356/73
See application file for complete search history.

(56) References Cited

U.S. PATENT DOCUMENTS

| 4,238,679 | A | * | 12/1980 | Macmillan ........... | G08B 17/113 |
|           |   |   |         |                     | 250/385.1 |
| 4,424,553 | A |   | 1/1984  | Marsocci et al.     |           |
| 4,564,762 | A |   | 1/1986  | Doherty et al.      |           |
| 4,851,819 | A |   | 7/1989  | Kawai et al.        |           |
| 5,751,218 | A |   | 5/1998  | Winterble et al.    |           |
| 6,433,700 | B1| * | 8/2002  | Malewski ............ | G08B 17/113 |
|           |   |   |         |                     | 340/628   |
| 6,953,936 | B2|   | 10/2005 | MacPherson, III et al. |       |

(Continued)

FOREIGN PATENT DOCUMENTS

CN         20104419 Y    4/2008
EP          2402920 B1   4/2014

(Continued)

OTHER PUBLICATIONS

European Search Report for European Application No. 201649619 dated Aug. 28, 2020.

(Continued)

*Primary Examiner* — Tarifur R Chowdhury
*Assistant Examiner* — Omar H Nixon
(74) *Attorney, Agent, or Firm* — Carlson, Gaskey & Olds, P.C.

(57) ABSTRACT

A photoelectric smoke detector, includes an optics cover that provides a smoke chamber that has a smoke chamber opening, a CO detector is mounted to the optics cover. An inner cover provides a first opening and a second opening. The first opening receives a portion of the CO detector and the second opening is aligned with the smoke chamber opening. A spoiler includes a U-shaped fin arrangement and is received against the inner cover.

20 Claims, 7 Drawing Sheets

(56) References Cited

U.S. PATENT DOCUMENTS

| | | |
|---|---|---|
| 9,666,048 B2 | 3/2017 | Fischer et al. |
| 9,685,058 B2 | 6/2017 | Schmidt et al. |
| 2013/0201024 A1 | 8/2013 | Greenwood et al. |
| 2017/0162019 A1* | 6/2017 | Cruse ...................... G01N 21/53 |
| 2018/0149581 A1* | 5/2018 | Lo ....................... G01N 21/0303 |
| 2018/0180540 A1* | 6/2018 | Iguchi ................... G01N 21/53 |

FOREIGN PATENT DOCUMENTS

| | | |
|---|---|---|
| EP | 2263219 B1 | 4/2017 |
| JP | 5819444 B2 | 11/2015 |
| RU | 177379 U1 | 2/2018 |
| WO | 9704429 A1 | 2/1997 |
| WO | 0007161 A1 | 2/2000 |
| WO | 2016186884 A1 | 11/2016 |

OTHER PUBLICATIONS

Examination Report for Indian Application No. 202014012992 dated Apr. 26, 2021.

* cited by examiner

US 11,074,796 B2

PHOTOELECTRIC SMOKE DETECTORS

CROSS-REFERENCE TO RELATED APPLICATION

This application claims priority to U.S. Provisional Application No. 62/827,612, which was filed on Apr. 1, 2019.

BACKGROUND

This application relates to smoke detectors, and more particularly photoelectric smoke detectors.

A photoelectric smoke detector includes a light source and a photoelectric receiver to detect whether or not smoke is present. Smoke is determined to be present when a change in the amount of light received at the photoelectric receiver exceeds a pre-determined value. Upon the smoke detector determining smoke is present, a fire alarm is tripped.

SUMMARY

A photoelectric smoke detector, according to an example of this disclosure includes an optics cover that provides a smoke chamber that has a smoke chamber opening, a CO detector is mounted to the optics cover. An inner cover provides a first opening and a second opening. The first opening receives a portion of the CO detector and the second opening is aligned with the smoke chamber opening. A spoiler includes a U-shaped fin arrangement and is received against the inner cover.

In a further example of the foregoing, the second opening has a contour substantially the same as a contour of a lip of the optics cover that provides the smoke chamber opening.

In a further example of any of the foregoing, the first opening is substantially T-shaped.

In a further example of any of the foregoing, the second opening is substantially D-shaped.

In a further example of any of the foregoing, the inner cover includes a divider portion that separates the first opening from the second opening.

In a further example of any of the foregoing, the U-shaped fin portion abuts the divider portion.

In a further example of any of the foregoing, the inner cover includes first and second projections angled to create a tapered path across an outer portion of the inner cover.

In a further example of any of the foregoing, the spoiler includes a ring portion, and a conical portion that extends from the ring portion. The U-shaped fin arrangement extends from the conical portion.

In a further example of any of the foregoing, the conical portion tapers as it extends toward the optics cover.

In a further example of any of the foregoing, an outer cover is attached to a base portion, and the outer cover includes an open entry portion.

In a further example of any of the foregoing, a gap is provided between the CO detector and the outer cover. The inner cover seals the gap from the entry portion to prevent smoke particles from entering the gap.

In a further example of any of the foregoing, the entry portion includes a first row of openings, a second row of openings, and a third row of openings. A bottom surface of the inner cover is flush with an upper surface of the first row of openings.

In a further example of any of the foregoing, an outer edge of the spoiler is received against a horizontal bar between the second row of openings and the third row of openings.

In a further example of any of the foregoing, the inner cover is heat staked to an outer cover.

In a further example of any of the foregoing, the inner cover is snap-fit to an outer cover.

In a further example of any of the foregoing, bug screen is positioned over the smoke chamber opening.

In a further example of any of the foregoing, the U-shaped fin arrangement extends to a plane that is provided at an outer lip of the smoke chamber, and the outer lip provides the smoke chamber opening.

In a further example of any of the foregoing, the U-shaped fin arrangement is open toward the CO detector.

In a further example of any of the foregoing, the U-shaped fin arrangement includes a first fin portion substantially parallel to the top of a central axis of the CO detector. A second fin portion and a third fin portion are substantially parallel to the second fin portion.

A photoelectric smoke detector according to an example of this disclosure includes a base portion, a circuit received on the base portion, an optics cover that is mounted to the base portion and provides a smoke chamber that has a smoke chamber opening. A CO detector is mounted to the optics cover. An inner cover provides a first opening and a second opening. The first opening receives a portion of the CO detector and the second opening is aligned with the smoke chamber opening. A spoiler includes a ring portion, a conical portion that extends from the ring portion toward the smoke chamber, and a U-shaped fin arrangement that extends from the conical portion. The spoiler is received against the inner cover. An outer cover is attached to a base portion. The outer cover includes an open entry portion. A gap is provided between the CO detector and the outer cover, and the inner cover seals the gap from the entry portion to prevent smoke particles from entering the gap.

These and other features may be best understood from the following specification and drawings, the following of which is a brief description.

DETAILED DESCRIPTION

Figure 1:
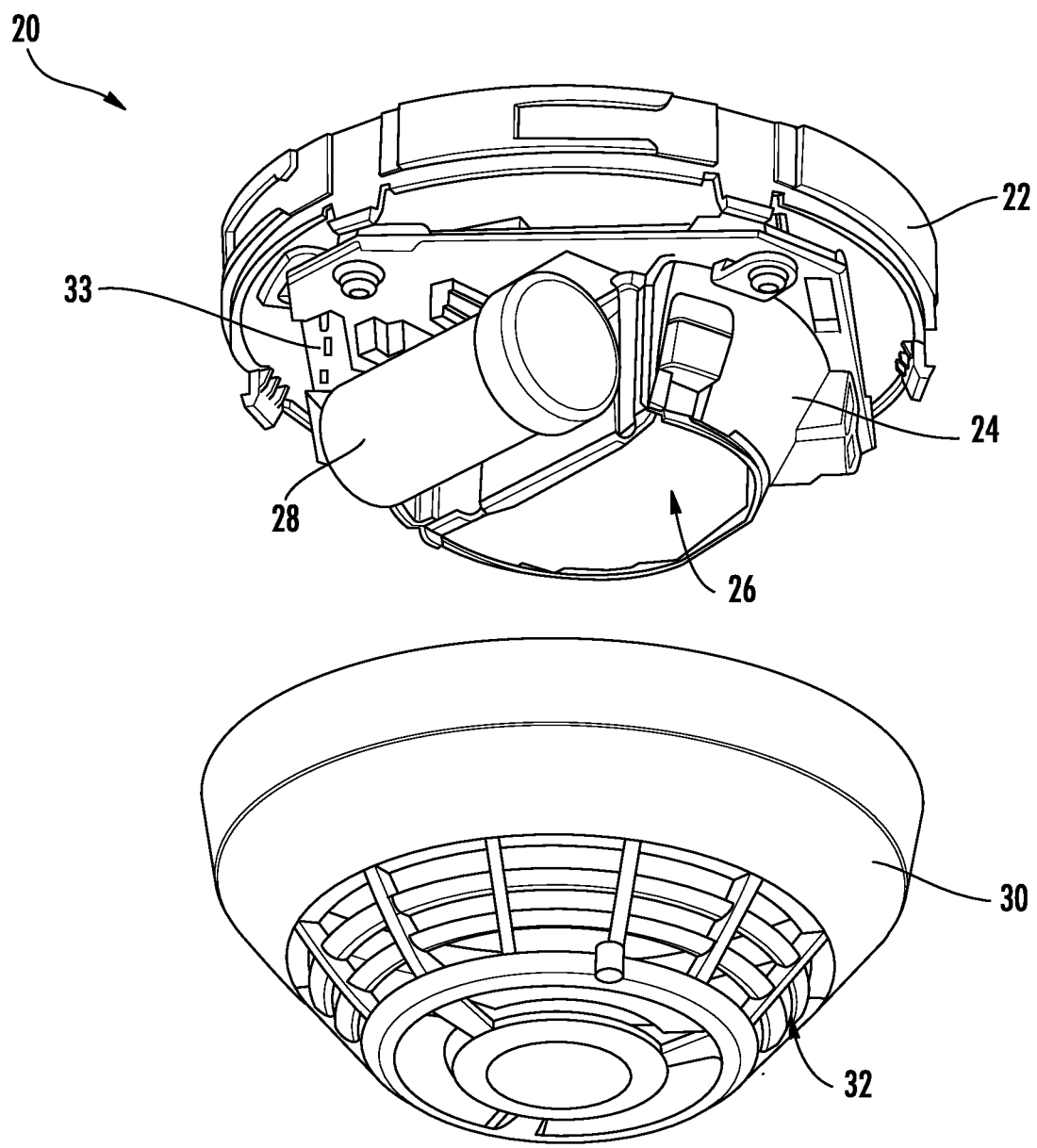
FIG. 1 illustrates a prior art smoke detector.

FIG. 1 illustrates a prior art smoke detector 20. A base portion 22 for mounting to a surface, such as a ceiling in some examples, is provided. An optics cover 24 is attached to the base portion 22 and provides a smoke chamber 26.

The example smoke detector 20 is a photoelectric smoke detector. In a photoelectric smoke detector, a light source (not shown) is aimed into the smoke chamber 26 at an angle away from a receiver (not shown). When smoke enters the chamber 26, smoke particles scatter the light from the light source onto the receiver, which then triggers an alarm. In some examples, the smoke detector 20 is a multi-wave multi-angle photoelectric smoke detector, as is known to include multiple photoelectric elements, such as several light sources and/or several receivers, to allow for multiple different types of signals.

A carbon monoxide (CO) detector 28 is mounted to the optics cover 24 outside of the smoke chamber 26 for detecting the presence of carbon monoxide. An outer cover 30 attaches to the base portion 22 but is shown as removed from the base portion 22 for ease of viewing. The outer cover 30 includes an open entry portion 32 for allowing smoke particles to enter the smoke detector 20 for detection. A circuit board 33 may be provided between the optics cover 24 and the base portion 22 to mechanically support and electrically connect electronic components of the smoke detector 20. The smoke detector 20 may include one or more inserts (not shown) for directing smoke particles from the entry portion 32 into the smoke chamber 26.

Directional orientations in this disclosure such as "above," "below," "top," "bottom," and the like are made with reference to ceiling mounted smoke detectors, but one of ordinary skill in the art having the benefit of this disclosure would recognize that smoke detectors mounted in other orientations may also benefit.

Applicant has identified that when smoke enters in certain directions of entry, such as directions of entry near the CO detector 28, prior art smoke detectors 20 are less efficient at directing smoke into the smoke chamber 26 for detection than when smoke enters from other directions.

Figure 2:
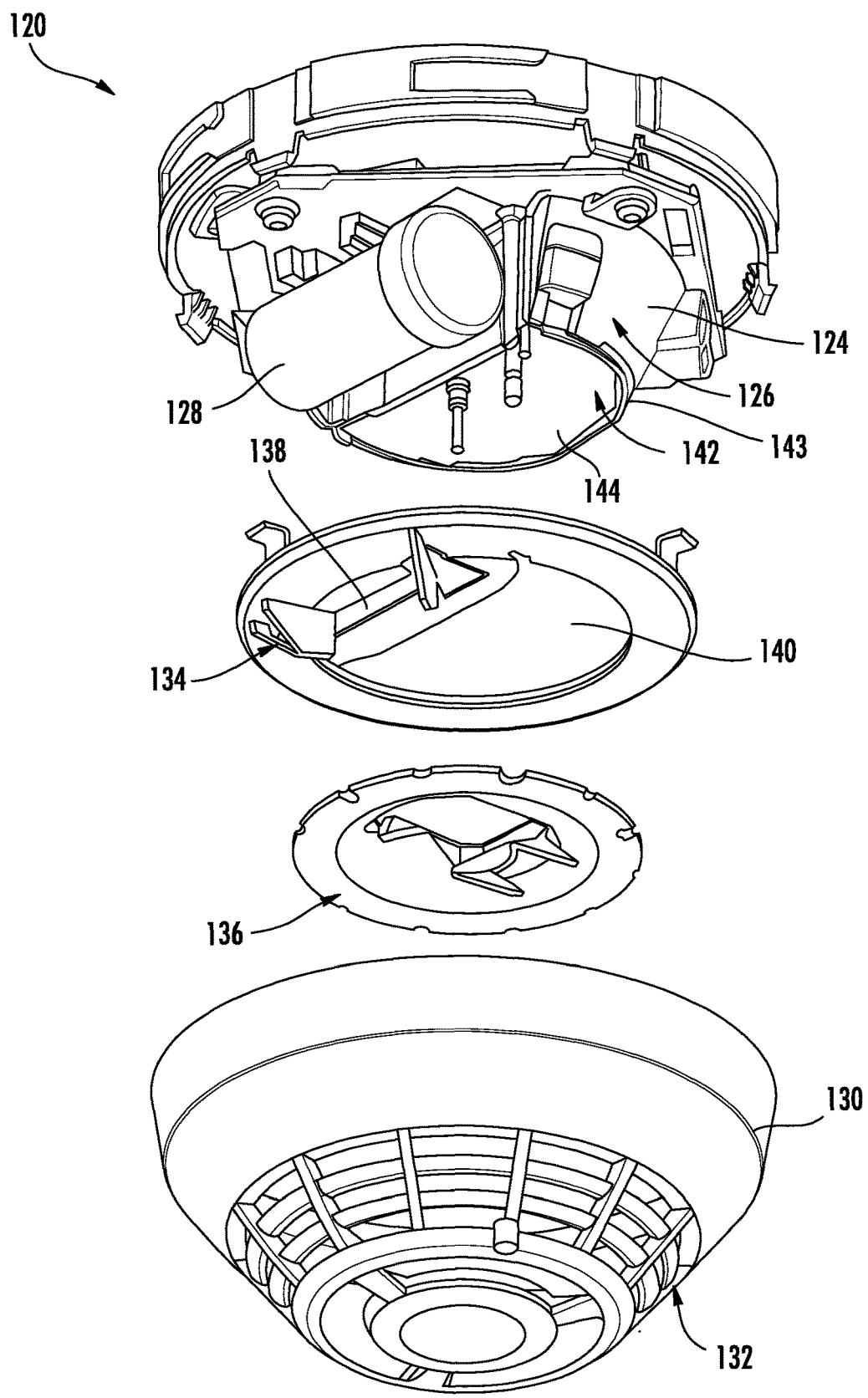
FIG. 2 illustrates an example smoke detector.

FIG. 2 illustrates an improved smoke detector 120. It should be understood that like reference numerals identify corresponding or similar elements throughout the several drawings. An inner cover 134 and a spoiler 136 are provided in the smoke detector 120 to uniformly direct smoke particles entering the smoke detector from all directions into the smoke chamber 126 and to prevent smoke particles from entering gaps outside of the smoke chamber 126.

In some examples, as shown, the inner cover 134 provides an opening 138 contoured to receive a portion of the CO detector 128 and an opening 140 positioned to align with the opening 142 of the optics cover 124. In some examples, as shown, the opening 138 is substantially T-shaped to accommodate two differently sized cylindrical portions of the CO detector 128. Other shapes may be used to accommodate differently shaped CO detectors in some examples. In some examples, as shown, the opening 140 has substantially the same contour as the opening 142. In some examples, as shown, the openings 140, 142 are substantially D-shaped. In some examples, as shown, the lip 143 of the opening 142 has substantially the same contour as the perimeter of the opening 140. Other shapes may be utilized to accommodate differently shaped smoke chambers in some examples. In some examples, a porous bug screen 144 may be placed over the opening 142 to prevent insects and the like from entering the smoke chamber 126.

The outer cover 130, the inner cover 134, and the spoiler 136 are shown in exploded form for ease of viewing, but, when assembled, the inner cover 134 is received against the CO detector 128 and the optics cover 124, and the spoiler 136 is received against the inner cover 134. As discussed further below, in some examples, the inner cover 134 may be attached to an inner surface of the outer cover 130.

In some examples, the inner cover 134 and the spoiler 136 are made of thermoplastic materials. In some examples the inner cover 134 and the spoiler 136 are made of acrylonitrile butadiene styrene (ABS).

Figure 3:
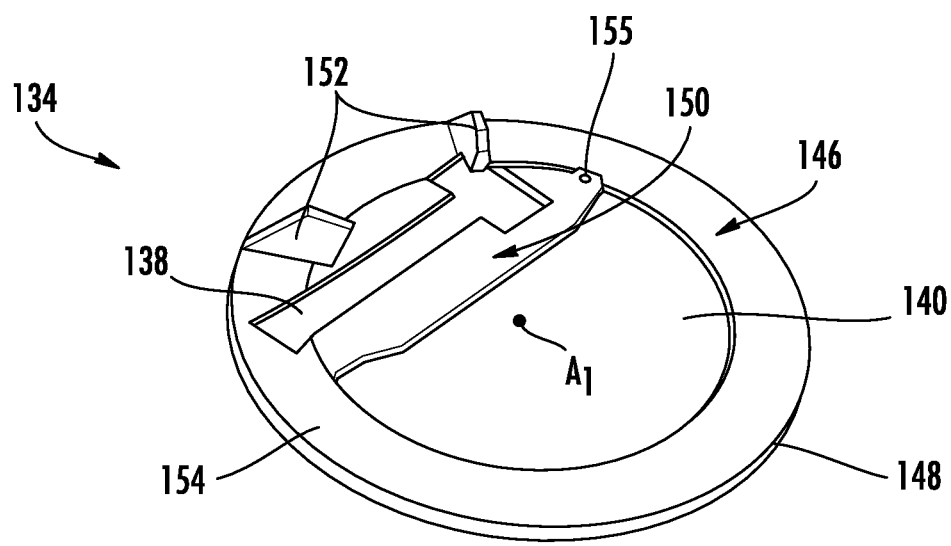
FIG. 3 illustrates an example inner cover of the example smoke detector of FIG. 2.

FIG. 3 illustrates the inner cover 134 shown in FIG. 2. The inner cover 134 includes an outer portion 146 providing an outer edge 148. The outer edge 148 of the inner cover 134 is shaped to be received by the outer cover 130 as described below with reference to FIG. 5. In some examples, the outer portion 146 may have a taper. In some examples, such as the example of FIG. 3, outer portion 146 may provide a circular outer edge 148 and the outer portion 146 may have a conical taper. A dividing portion 150 separates the opening 138 from the opening 140. The inner cover 134 may further include projections 152 extending from a bottom surface 154. The inner cover 134 may be positioned about a central axis A1 relative to the outer edge 148 in some examples. As shown, the axis A1 extends through the opening 140 in some examples. The inner cover 134 may include a light pipe aperture 155 for receiving a light pipe indicator 157 (see FIG. 4).

Figure 4:
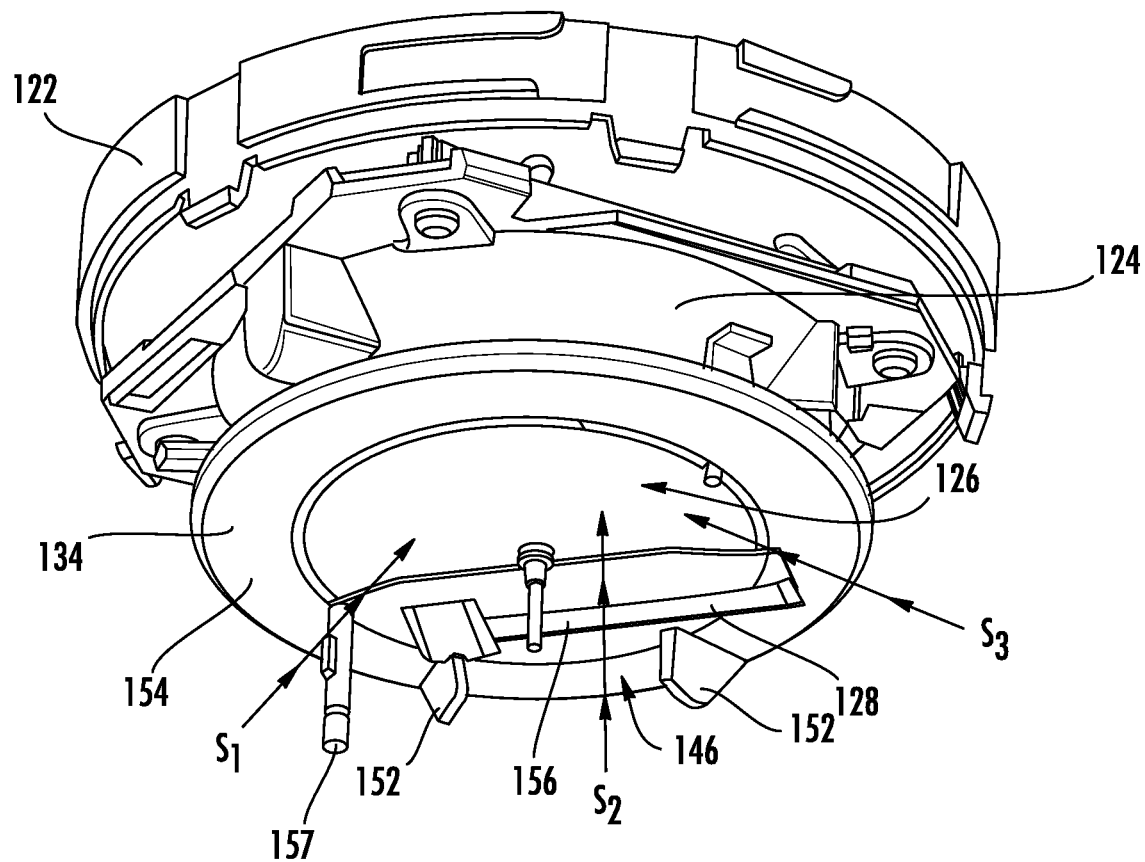
FIG. 4 illustrates a portion of the example smoke detector of FIG. 2.

FIG. 4 illustrates the inner cover 134 received against the optics cover 124. The bottom surface 154 faces away from the base portion 122 when assembled. In some embodiments a light pipe 157 received into the inner cover 134 may direct light from within the detector 120, such as from a light-emitting diode or other light source, to the outside of the detector 120, or may direct light received from outside of the detector 120 to a sensor or other device within the detector 120 and above inner cover 134. The inner cover 134 is received in abutment against the lip 143 (not shown; see FIG. 2) and the CO detector 128, such that smoke particles moving across the bottom surface 154 are directed toward the smoke chamber 126.

As shown schematically, smoke particles S1, S3 entering the smoke detector 120 move across the bottom surface 154 of the inner cover 134 and into the smoke chamber 126. Smoke particles S2 entering in directions near the CO detector 128 move across the bottom surface 154 and the bottom surface 156 of the CO detector 128 before entering the smoke chamber 126. The projections 152 are angled to direct smoke particles S2 toward the smoke chamber 126 by providing a tapered path across the bottom surface 154 of the outer portion 146 of the inner cover 134 before the particles move over the CO detector 128. The inner cover 134, the optics cover 124, and CO detector 128 are engaged in a sealing manner to prevent gaps within the smoke detector 120 but outside of the smoke chamber 126 that may trap smoke S1, S2, S3 outside of the smoke chamber 126.

Figure 5:
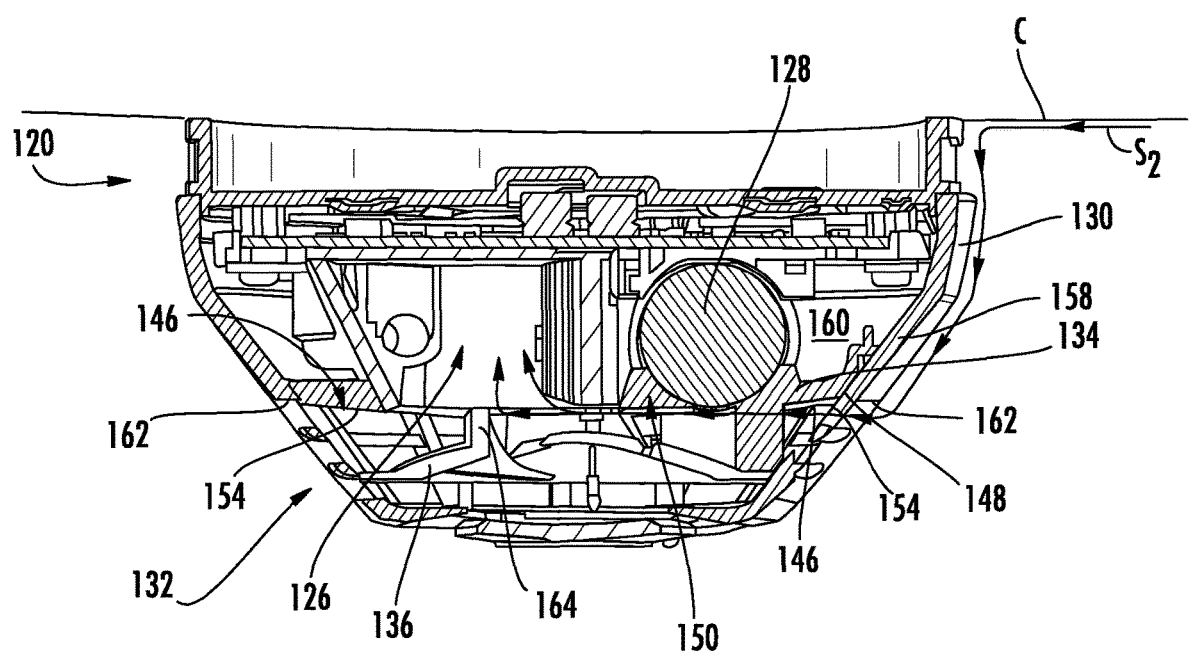
FIG. 5 illustrates a cross sectional view of the example smoke detector.

FIG. 5 illustrates a cross-sectional view of the example smoke detector 120. The outer edge 148 of the inner cover 134 is received against the inner surface 158 of the outer cover 130 to prevent smoke from entering gaps other than the smoke chamber 126, such as the gap 160 between the CO detector 128 and the outer cover 130 in some examples. In some examples, as shown, the bottom surface 154 of the outer portion 146 is substantially flush with the upper surface 162 of the entry portion 132.

As shown schematically in FIG. 5 with reference back to FIG. 4, smoke particles S2 may move across a ceiling C, down the outer surface of the outer cover 130, into the smoke detector 120 through the entry portion 132 and across the surface 162, across the bottom surface 154 at the outer portion 146, across the CO detector 128, across the bottom surface 154 at the dividing portion 150 and into the smoke chamber 126. Some smoke particles may deflect off a fin 164 of the spoiler 136 toward the smoke chamber 126, as discussed further below.

Figure 6:
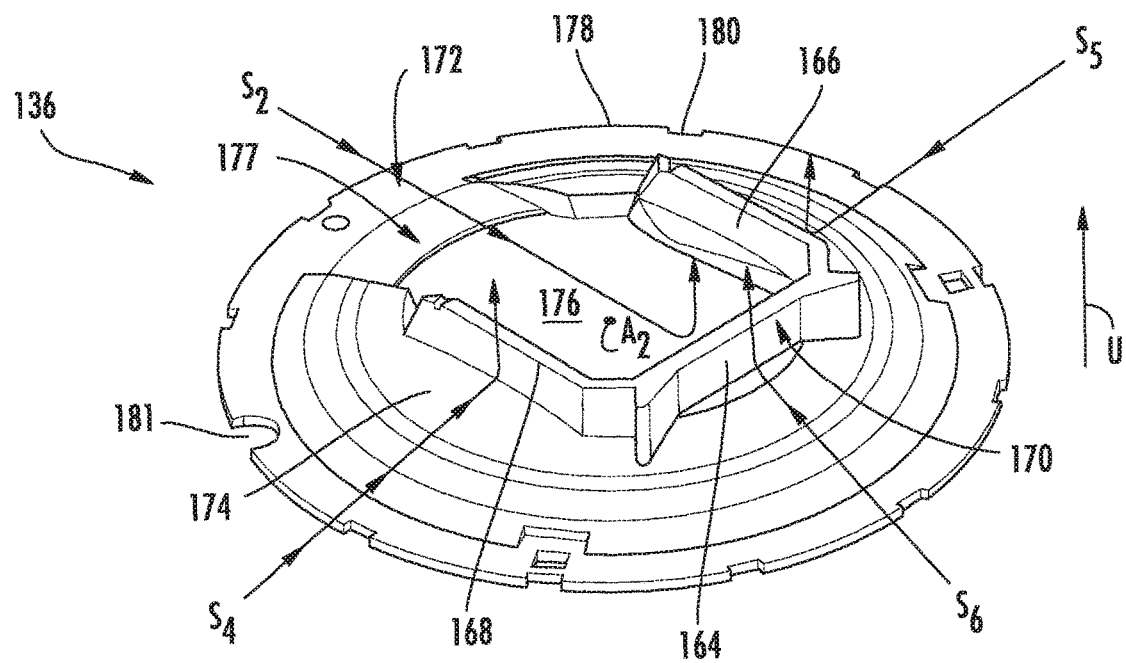
FIG. 6 illustrates an example spoiler for the example smoke detector.

FIG. 6 illustrates the spoiler 136 oriented in the upward direction U as it would be within a ceiling mounted configuration of the smoke detector 120. Fins 166 and 168 connect to and extend from the fin 164 to form a U-shaped fin arrangement 170. The U-shaped fin arrangement 170 is positioned to be open toward the CO detector 128 (see FIG. 5). That is, the open side of the U-shaped fin arrangement 170 is nearer the CO detector 128 than the fin 164. One or more of the fins 164, 166, 168 of the U-shaped fin arrangement 170 may include straight portions.

The spoiler 136 includes a ring portion 172 and a conical portion 174 extending upwardly from the ring portion 172. The U-shaped fin arrangement 170 extends from the conical portion 174. The spoiler 136 provides an opening 176 inward (relative to the outer edge 178) of the U-shaped fin arrangement 170. The U-shaped fin arrangement 170 is open toward a void 177 in the conical portion 174 that extends from the opening 176. The ring portion 172 includes an outer edge 178, which may have a number of notches 180 for receiving posts (not shown) of the entry portion 132. The ring portion 172 may be positioned about a central axis A2. In the illustrative example, when assembled the axis A2 of the ring portion 172 aligns with the axis A1 of the outer portion 146 (see FIG. 3). The spoiler 136 may include a light pipe groove 181 for receiving a light pipe indicator 157 (shown in FIG. 4).

As shown schematically in FIG. 6 with reference back to FIGS. 4 and 5, smoke particles S2 may deflect off the fin 164 and into the smoke chamber 126 (not shown). Smoke particles S4 may move along the ring portion 172 and conical portion 174 and deflect off the fin 168 and upward into the smoke chamber 126. Smoke particles S5 may move along the ring portion 172 and conical portion 174 and deflect off the fin 166 and upward into the smoke chamber 126. Smoke particles S6 may move along the ring portion 172 and conical portion 174 and deflect off the fin 164 and upward into the smoke chamber 126.

Figure 7:
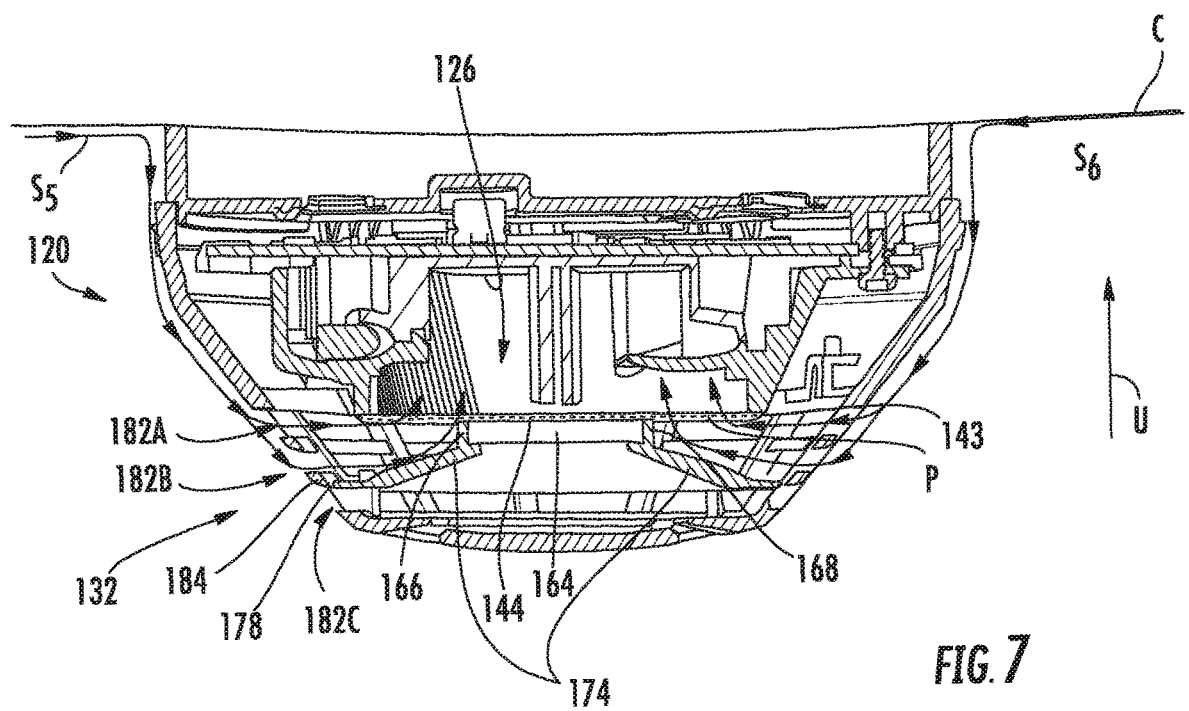
FIG. 7 illustrates a cross sectional view of the example smoke detector.

FIG. 7 shows a cross sectional view of the example smoke detector 120, showing smoke particle paths S5 and S6, with reference to FIG. 6. As shown, the example conical portion 174 tapers as it extends upward toward the smoke chamber 126 to form a continuous surface from the entry portion 132 to the leading edge of the chamber 126. The outer edge 178 of the spoiler 136 is received against the inner surface 158 of the outer cover 130 at the entry portion 132. In some examples, as shown, the entry portion 132 provides three rows of openings 182A, 182B, and 182C, and the edge 178 is received against the horizontal bar 184 between the lower two rows 182B and 182C. In some examples, as shown, the fins 164, 166, 168 extend to a plane P at the lip 143 of the smoke chamber 126. In some examples, as shown the bug screen 144 may be positioned along the plane P. Other heights can be utilized in some examples. The fins 164, 166, 168 extend from the conical portion 174 upward toward the smoke chamber 126.

Figure 8:
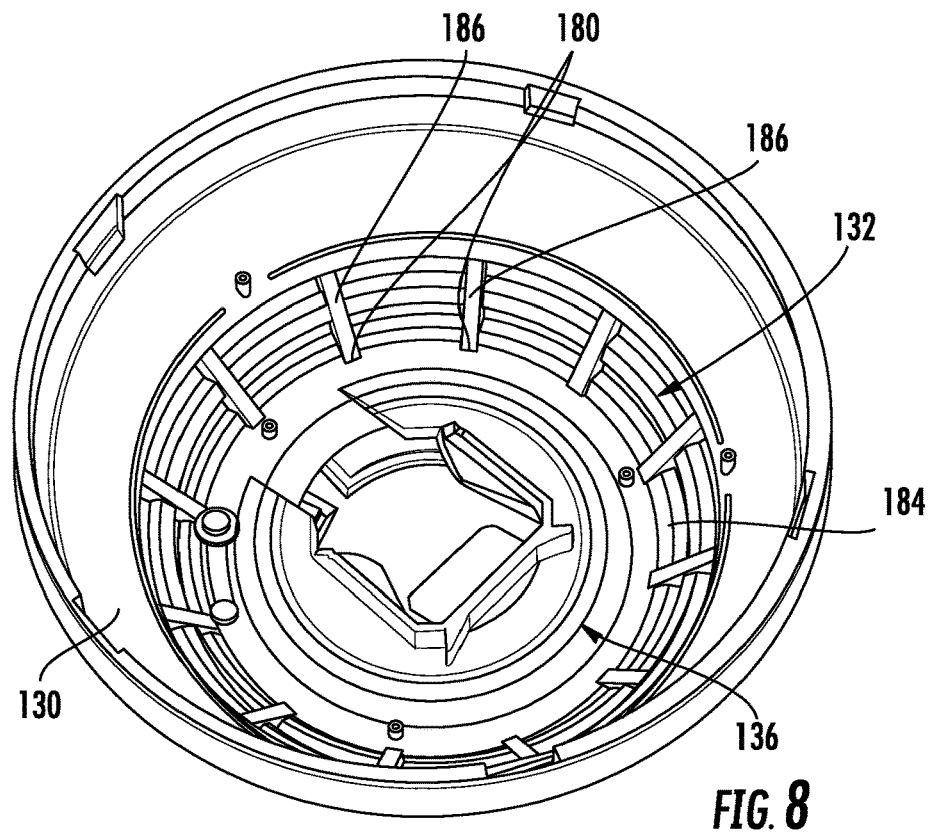
FIG. 8 illustrates the example spoiler of FIG. 6 received within an example outer cover.

FIG. 8 illustrates the spoiler 136 received against the bar 184 of the entry portion 132 of the outer cover 130. The notches 180 receive the posts 186 of the entry portion.

Figure 9:
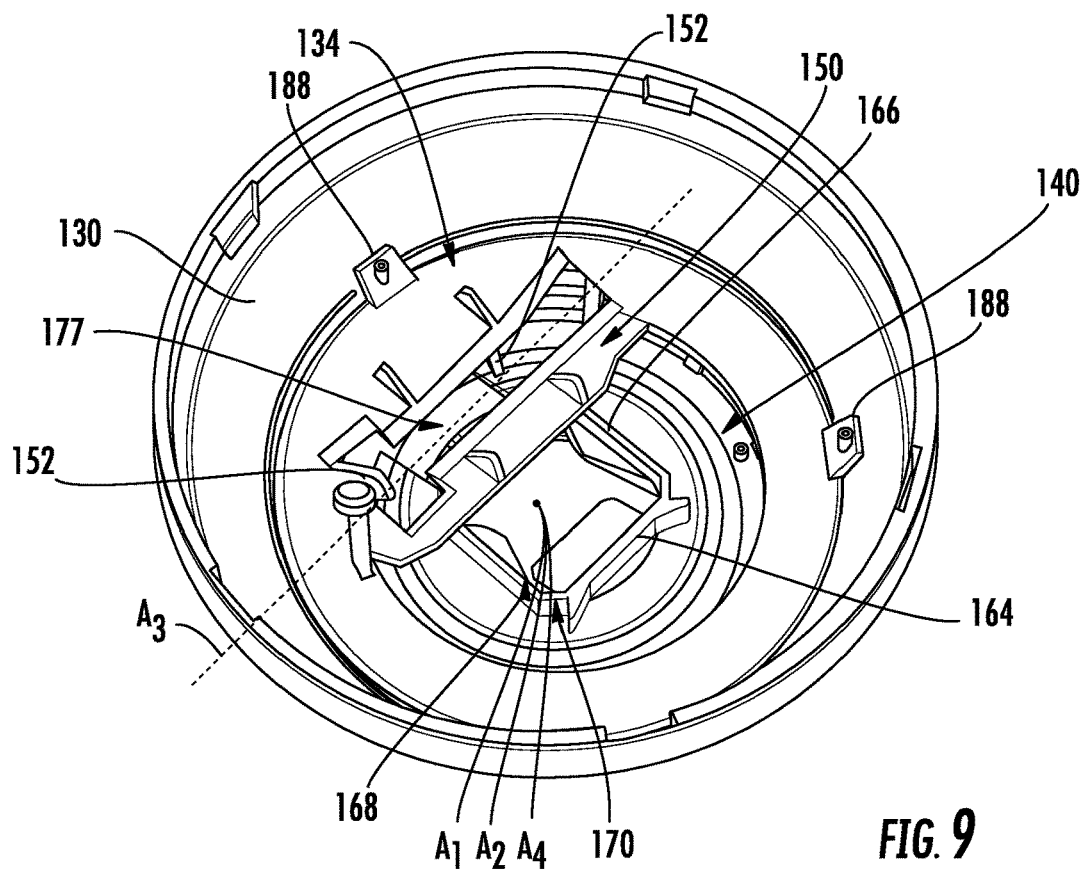
FIG. 9 illustrates the example inner cover of FIG. 3 received within the example outer cover.

FIG. 9 illustrates the inner cover 134 attached to the outer cover 130. In some examples, the inner cover 134 is heat staked to the outer cover 130. In some examples, the inner cover 134 is snap fit to the outer cover 130. In some examples, the inner cover 134 includes tabs 188 for attachment to the outer cover 130.

When assembled, the fin 164 is substantially parallel to the central axis A3 of the CO detector 128 (not shown). In some examples, as shown, the fins 166 and 168 are substantially parallel to one another. As shown, the projections 152 provide a tapered path toward the opening of the U-shaped fin arrangement 170. The void 177 is positioned within the same circumferential region as the CO detector 128 (not shown). The ends of the fins 166, 168 may be received against the dividing portion 150. The outer cover 130 may be positioned relative to a central axis A4, such that the axes A1, A2, and A4 are substantially aligned.

The example smoke detector 120 utilizes Brownian motion principles for the motion of smoke particles within air. Brownian principles describe the ability of small smoke particles to remain suspended due to interactions with the atmosphere with motions that are energetic enough to resist the pull of gravity which would force these particles to fall to earth. The inner cover 134 seals gaps and prevents smoke particles from settling within the gaps instead of moving into the smoke chamber 126. The placement and angling of the various surfaces, fins, and projections of the inner cover 134 and spoiler 136 in the illustrative example direct smoke particles into the smoke chamber 126 in an improved, uniform manner relative to the prior art. Detection among various angles of entry relative to the horizontal plane of the smoke detector 120 is more uniform as compared to prior art smoke detectors.

Figure 10:
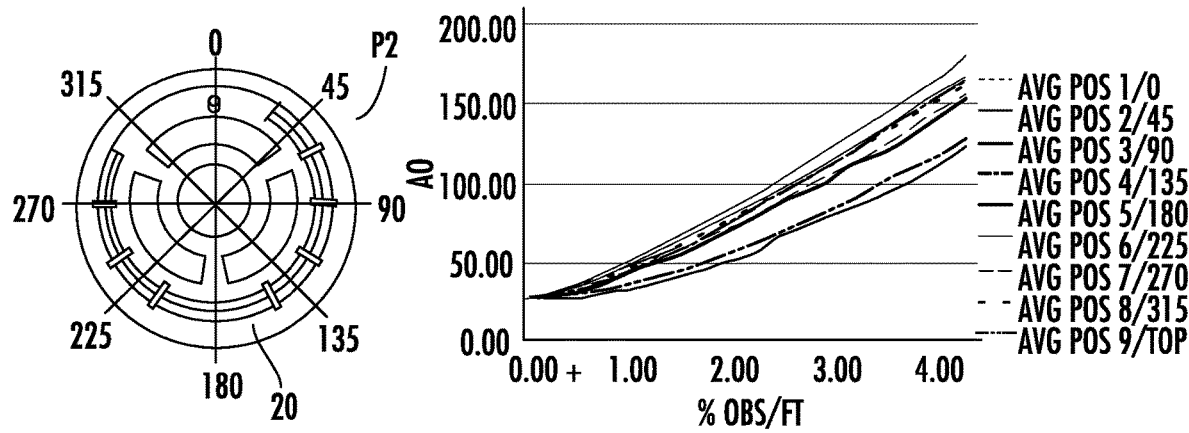
FIG. 10 illustrates a performance graph of the prior art smoke detector of FIG. 1.

FIG. 10 illustrates a graph, for the various positions shown in the horizontal plane P2 of the prior art smoke detector 20, of smoke in air denoted by obscuration per foot (OBS/ft) against the analog signal converted to a digital output (AD) of refracted light detected by the photodiode from the forward scatter infrared LED. The Forward (F) infrared (IR) LED emits radiation in the smoke chamber 26 and some of this radiation is scattered in the forward direction towards the photodiode which is a direct function of obscuration % of smoke. Each of the curves represent the behavior of a single smoke detector for its specified angle of entry of the smoke path into the prior art smoke detector 20. A wide variation of signal response is observed. That is, as seen, there was significant variance of detection among the various angles of entry into the prior art smoke detector 20.

Figure 11:
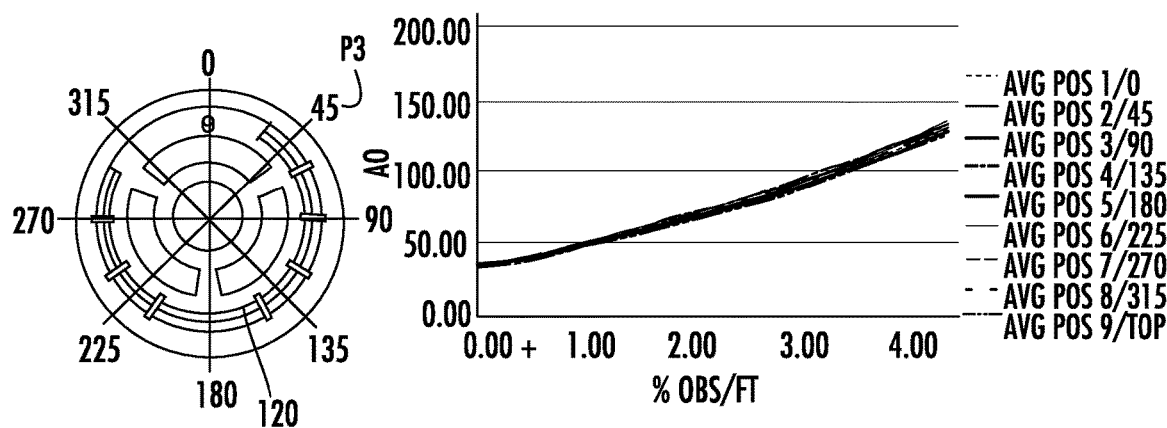
FIG. 11 illustrates a performance graph of the example smoke detector.

FIG. 11 illustrates a similar graph for the corresponding various positions in the horizontal plane P3 of the example smoke detector 120. As seen, there was more uniform detection between the various angles of entry into the example smoke detector 120. The inner cover 134 and the spoiler 136 of the illustrative example facilitate a uniform signal regardless of orientation of smoke entry into the example smoke detector 120. Thus, the detector 120 is more equally sensitive in all orientations. One of ordinary skill in the art having the benefit of this disclosure would recognize that certain modifications could be made to the illustrative example, while still achieving similar benefits.

Although the different examples are illustrated as having specific components, the examples of this disclosure are not limited to those particular combinations. It is possible to use some of the components or features from any of the examples in combination with features or components from any of the other examples.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A photoelectric smoke detector, comprising:
an optics cover providing a smoke chamber having a smoke chamber opening;
a CO detector mounted to the optics cover;
an inner cover providing a first opening and a second opening, wherein the first opening receives a portion of the CO detector and the second opening is aligned with the smoke chamber opening;
a spoiler including a U-shaped fin arrangement and received against the inner cover.

2. The smoke detector as recited in claim 1, wherein the second opening has a contour substantially the same as a contour of a lip of the optics cover providing the smoke chamber opening.

3. The smoke detector as recited in claim 1, wherein the first opening is substantially T-shaped.

4. The smoke detector as recited in claim 3, wherein the second opening is substantially D-shaped.

5. The smoke detector as recited in claim 1, wherein the inner cover includes a divider portion that separates the first opening from the second opening.

6. The smoke detector as recited in claim 1, wherein the U-shaped fin portion abuts the divider portion.

7. The smoke detector as recited in claim 1, wherein the inner cover includes first and second projections angled to create a tapered path across an outer portion of the inner cover.

8. The smoke detector as recited in claim 1, wherein the spoiler includes
a ring portion, and
a conical portion extending from the ring portion, and the U-shaped fin arrangement extends from the conical portion.

9. The smoke detector as recited in claim 8, wherein the conical portion tapers as it extends toward the optics cover.

10. The smoke detector as recited in claim 1, comprising an outer cover attached to a base portion, wherein the outer cover includes an open entry portion.

11. The smoke detector as recited in claim 10, wherein a gap is provided between the CO detector and the outer cover, and the inner cover seals the gap from the entry portion to prevent smoke particles from entering the gap.

12. The smoke detector as recited in claim 10, wherein the entry portion includes a first row of openings, a second row of openings, and a third row of openings, and a bottom surface of the inner cover is flush with an upper surface of the first row of openings.

13. The smoke detector as recited in claim 12, wherein an outer edge of the spoiler is received against a horizontal bar between the second row of openings and the third row of openings.

14. The smoke detector as recited in claim 1, wherein the inner cover is heat staked to an outer cover.

15. The smoke detector as recited in claim 1, wherein the inner cover is snap-fit to an outer cover.

16. The smoke detector as recited in claim 1, comprising:
a bug screen positioned over the smoke chamber opening.

17. The smoke detector as recited in claim 1, wherein the U-shaped fin arrangement extends to a plane provided at an outer lip of the smoke chamber, and the outer lip provides the smoke chamber opening.

18. The smoke detector as recited in claim 1, wherein the U-shaped fin arrangement is open toward the CO detector.

19. The smoke detector as recited in claim 1, wherein the U-shaped fin arrangement includes:
a first fin portion substantially parallel top a central axis of the CO detector,
a second fin portion, and
a third fin portion substantially parallel to the second fin portion.

20. A photoelectric smoke detector, comprising:
a base portion;
a circuit received on the base portion;
an optics cover mounted to the base portion and providing a smoke chamber having a smoke chamber opening;
a CO detector mounted to the optics cover;
an inner cover providing a first opening and a second opening, wherein the first opening receives a portion of the CO detector and the second opening is aligned with the smoke chamber opening;
a spoiler including a ring portion, a conical portion extending from the ring portion toward the smoke chamber, and a U-shaped fin arrangement extending from the conical portion, the spoiler being received against the inner cover; and
an outer cover attached to a base portion, wherein the outer cover includes an open entry portion, wherein a gap is provided between the CO detector and the outer cover, and the inner cover seals the gap from the entry portion to prevent smoke particles from entering the gap.

* * * * *